United States Patent [19]

Hokazono et al.

[11] Patent Number: 5,001,143

[45] Date of Patent: Mar. 19, 1991

[54] PHARMACEUTICAL COMPOSITION FOR PROPHYLACTIC AND PREVENTIVE OF KETOSIS OF LIVESTOCKS

[75] Inventors: Akio Hokazono, Yokohama; Masahiro Shimosako, Kawaguchi; Tatsuyoshi Sugimoto, Hashimoto; Takehiro Shimada, Amagasaki; Masahiro Hayashi, Sakai, all of Japan

[73] Assignee: Nihon Nohyaku Co., Ltd., Tokyo, Japan

[21] Appl. No.: 399,447

[22] Filed: Aug. 28, 1989

Related U.S. Application Data

[63] Continuation of Ser. No. 635,163, Jul. 24, 1984, abandoned.

[30] Foreign Application Priority Data

Aug. 1, 1983 [JP] Japan ................ 58-139488

[51] Int. Cl.$^5$ ................ A61K 31/38; A61K 31/385
[52] U.S. Cl. ................ 514/430; 514/440; 514/441
[58] Field of Search ................ 514/430, 440, 441

[56] References Cited

U.S. PATENT DOCUMENTS

| | | | |
|---|---|---|---|
| 4,022,907 | 5/1977 | Taninaka et al. | 514/430 |
| 4,080,466 | 3/1978 | Taninaka et al. | 514/441 |
| 4,080,467 | 3/1978 | Taninaka et al. | 514/441 |
| 4,118,506 | 10/1978 | Taninaka et al. | 514/440 |

FOREIGN PATENT DOCUMENTS

| | | |
|---|---|---|
| 332310 | 5/1984 | Fed. Rep. of Germany . |
| 2312038 | 12/1976 | France . |
| 2313037 | 12/1976 | France . |
| 2313041 | 12/1976 | France . |
| 50916 | 12/1982 | Japan . |
| 185591 | 3/1983 | Japan . |

OTHER PUBLICATIONS

The Merck Veterinary Manual, Fifth Ed. (1979) Pages 194–198, Merck & Co. Rahway, N.J.

*Primary Examiner*—Frederick E. Waddell
*Attorney, Agent, or Firm*—Cushman, Darby & Cushman

[57] ABSTRACT

A pharmaceutical composition for prophylactic and preventive of ketosis of livestocks which contains a dithia derivative represented by the general formula (I),

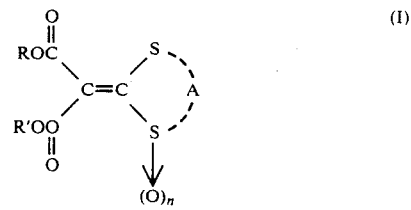

wherein R and R' may be the same or different and are each individually a lower alkyl group, n is an integer of 0, 1 or 2; and A is a group of the formula, —CH$_2$—,

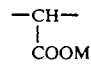

(wherein M is a hydrogen atom or a salt-forming residue), —CH=CH—, —CH$_2$—CH$_2$—,

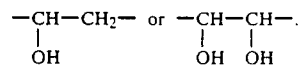

6 Claims, No Drawings

PHARMACEUTICAL COMPOSITION FOR PROPHYLACTIC AND PREVENTIVE OF KETOSIS OF LIVESTOCKS

This is a continuation of Application No. 06/635,163, filed July 25, 1984 on abandoned, which was abandoned upon the filing hereof.

FIELD OF THE INVENTION

The present invention relates to pharmaceutical composition for prophylactic and preventive of ketosis of livestocks. More particularly, the present invention relates to pharmaceutical composition for prophylactic and preventive of ketosis of livestocks which contains a dithia derivative represented by the general formula (I):

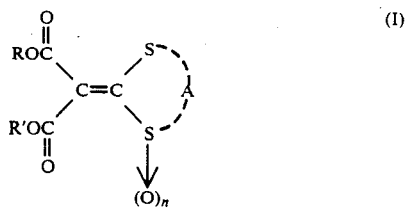

wherein R and R' may be the same or different and are individually a lower alkyl group; n is an integer of 0, 1 or 2; and A is a group of the formula, —CH$_2$—,

(M is a hydrogen atom or a salt-forming residue), —CH=CH—, —CH$_2$—CH$_2$—,

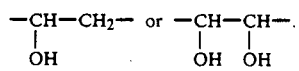

DESCRIPTION OF THE PRIOR ART

Part of the dithia derivatives represented by the general formula (I) are already known as treating agents for curing hepatopathy of humans and animals, in Japanese Patent Publication Nos. 18576/1981 to 18579/1981, and also known as for agricultural-horticultural disinfectants in Japanese Patent Publication Nos. 44526/1969 and 34883/1976.

The pharmacological activity which is the part of biological activities of the dithia derivatives represented by the general formula (I) exhibits as a curing agent for hepatopathy has been thought to be as follows. That is, when the function of liver is damaged by a factor such as alcohol, malnutrition, viruses, chemicals, toxicants, bile duct obstruction, hepatic circulation dyscrasia or the like or their combination and as a consequence there appears a disease such as fatty liver, toxipathic hepatisis, alcoholic hepatitis, viral hepatitis, congested liver, hepatopathy due to cholestasis, icterus, hepatocirrhosis caused by these diseases or the like or their combination, the part of the dithia derivatives represented by the general formula (I) activate protein synthesis at lever and prevents liever fibrosis, whereby the functions of liver are generated and liver cells are reactivated and finally dyshepatia is alleviated or cured.

Meanwhile, ketosis in livestocks, particularly in dairy cows is characterized in that dairy cows contracting this disease have poor appetite, their body weight decrease, and they produce milk of lower quality in a lesser quantity. The number of the dairy cows hitherto seized by ketosis has been numerous. Nevertheless, the cause of this disease as well as the mechanism of appearance of the disease has not been clarified and accordingly no reliable method for curing ketosis has been established. With respect to the process up to ketosis appearance, the following explanation is made in JUI-BYORIGAKU-TOKURON (A special issue on pathology of veterinary science) by YAMAGIWA.

"The mechanism of ketosis appearance has not fully been clarified. Ketosis is analysed below as a phenomenon. Firstly, digestion in rumen is focused. In the rumen, carbohydrates are digested by the enzymatic activity of many microorganisms. Volatile fatty acids (i.e., acetic acid, butyric acid and propionic acid) are formed and absorbed becoming energy sources for cows. Of these fatty acids, acetic acid and butyric acid are converted into ketone bodies, while propionic acid is not converted into a ketone body but is used for production of glycogen at liver. Of the volatile fatty acids formed, the first two acids (acetic acid and butyric acid) occupy 80% and the last acid (propionic acid) 20%. Parental cows store glycogen at their fetal livers toward the end of pregnancy and, after delivery, send glycogen into milk; hence, in parental cows before and after delivery, the normal balance of glycogen is collapsed.

When lactation starts, milk production takes place suddenly and more nutrients are required for enabling the production. Increased supply and digestion of carbohydrates in rumen becomes necessary. In cows in the midst of lactation, metabolism of carbohydrates becomes smooth only when nutritional demand and intake are balanced. Hence, in cows in the period from the end of pregnancy to the early stage of lactation, health can be maintained only when the above-mentioned conditions are satisfied. In cows in such a period, nutritional demand is very high, however, it is self-controlled so that the heperemia of breast can be prevented. As delivery approaches, the blood sugar level of cows continues to decrease and, after delivery, it further decreases sharply and the low level lasts for a certain period. In this period, ketone bodies are present in bloods of cows. Ketone bodies are also present in normal animals, however, the amount is negligible to 5 to 6 mg per cent in their bloods and negligible to 15 to 16 mg per cent in their urines. With these amounts, no ketosis appears.

Clinical ketosis rarely appears when dairy cows have a constant appetite and are fed with appropriate feeds. However, if ketone bodies are accumulated in blood in a concentration of 80 mg per cent and excreted in urine in a concentration of 550 mg per cent and furthermore sugar level in blood decreases down to 50% (20 to 30 mg per cent), that is, ketonemia, ketouria and hypoglycemia are present concurrently, there appears clinical ketosis."

As explained above, ketosis is a diseases wherein dairy cows have lower appetite, their carbohydrates metabolism becomes non-smooth, acetic acid and butyric acid are converted into respective ketone bodies and are accumulated in their bloods and excreted in their urines, in high concentrations, and their expired airs and excreted urines have acetone odors.

For prevention of ketosis of cows, studies have been made from the aspect of controlled breeding such as use of a special feed for the period before and after delivery. For therapy of ketosis, studies have been made from the following aspects.

(1) Increase of nutritional supply and enhancement of digestive ability in rumen
  (a) Administration of digestive
  (b) Supplementation of nutrients (glucose, sodium propionate, etc.)
(2) Enhancement of carbohydrates-metabolizing ability of cows by administration of, for example, a vitamin such as $B_{12}$ or the like, a hepatotonic such as methionine, and a hormone. None of these therapeutic studies has brought about a noticeable effect.

Based on the results of these past therapeutic studies for ketosis of cows, the present inventors made extensive research on effects of nutritional physiology, administration of drugs, etc. on ketosis conditions of cows. As a result, it was found that the diathia derivatives represented by the general formula (I) reduce abnormal accumulation of ketone bodies during ketosis and have a noticeable prophylactic and preventive effects for ketosis. The present invention was completed by these findings.

In the symbol A of the general formula (I), M as a salt-forming residue is specifically a sodium atom, a potassium atom, an ammonium group, an organic amine group, or the like.

Typical examples of the dithia derivatives represented by the general formula (I) and their toxicities are as follows.

PHARMACOLOGICAL TESTS

Pharmacological tests for the active ingredient of pharmaceutical composition of the present invention were conducted, by making the active ingredient into granules as in Example 1 and forcibly administering the granules orally to cows seized by ketosis in a predetermined dose once daily for 6 weeks. Examinations of various check items were made for bloods and urines taken from the cows before and 1, 3 and 6 weeks after the administration. In serum biochemical diagnosis, bloods were taken, coagulated and then subjected to centrifugation (3,000 rpm, 15 min.) to obtain respective serums and these serums were used. Blood sugar level was determined by a method using a glucose oxidase; free fatty acids were determined by an ACS-ACO-POD method; and ketone bodies in blood were determined by a diffusion colorimetry using salicyl aldehyde (THIN-ROBERTSON method). Ketone bodies in urine were determined by the use of Labstix (Sankyo Miles).

As shown in Table 1, high levels of acetoacetic acid in blood before the administration which are characteristic of ketosis were reduced by the administration of a dithia derivative of the present invention and returned to the normal values in 3 to 6 weeks after the administration. High levels of free fatty acids in blood which are generally used as an indication of ketosis returned to the normal values in 3 to 6 weeks after administration. Ketone bodies in urine were hardly detected in 3 weeks after the administration. As a common phenomenon,

| Compound No. | A | n | R | R' | M.P. °C. | Toxicity $LD_{50}$ (male mice) mg/kg |
|---|---|---|---|---|---|---|
| 1 | $-CH_2-$ | 0 | i-$C_3H_7$ | i-$C_3H_7$ | 104–105 | >5,000 |
| 2 | $-CH_2-$ | 0 | $C_2H_2$ | i-$C_3H_7$ | 37–39 | >5,000 |
| 3 | $-CH-$<br>|<br>COOH | 0 | i-$C_3H_7$ | i-$C_3H_7$ | 170–171 | >5,000 |
| 4 | $-CH=CH-$ | 0 | i-$C_3H_7$ | i-$C_3H_7$ | 55–57 | 3,120 |
| 5 | $-CH=CH-$ | 0 | $C_2H_5$ | $C_2H_5$ | 113 | 4,900 |
| 6 | $-CH_2-CH_2-$ | 0 | i-$C_3H_7$ | i-$C_3H_7$ | 54.5–55 | 1,350 |
| 7 | $-CH_2-CH_2-$ | 1 | i-$C_3H_7$ | i-$C_3H_7$ | 78–83 | >6,000 |
| 8 | $-CH_2-CH-$<br>|<br>OH | 0 | i-$C_3H_7$ | i-$C_3H_7$ | 73–74 | >6,590 |
| 9 | $-CH-CH-$<br>|   |<br>OH   OH | 0 | i-$C_3H_7$ | i-$C_3H_7$ | 132.5 | |

When the active ingredient contained in the pharmaceutical composition of the present invention is administered to livestock, it is administered (a) singly, as it is, (b) in the form of a mixture with a feed, or (c) in an ordinary administration unit form such as powder, granule, tablet, sugar coated tablet, capsule, suspension, ampule, injection preparation or the like. The dose of pharmaceutical composition according to the present invention can vary depending upon the kind of domestic aniaml, age, body weight, stage of disease, condition of disease, etc. In general, it is advantageous that 0.1 to 250 mg, preferably 1 to 100 mg per kg of body weight per day is orally administered and 0.01 to 250 mg per kg of body weight per day is administered parenterally.

the cows administered with the test dithia derivative recovered appetite gradually and had normal appetite in 3 weeks. Their lactation amounts also returned to normal levels in 3 to 4 weeks after the administration.

As is obvious from these results, the active ingredient of the present invention are highly effective for cows afflicted with ketosis.

Among the dithia derivatives represented by the general formula (I), those having i-propyl groups as to the symbols R and R'; and A is a group of the formula $-CH=CH-$ or $-CH_2-CH_2-$ are effective. Particularly, diisopropyl 1,3-dithiolan-2-ylindene malonate is most effective.

TABLE 1

Results of Administration of Present Invention Compounds to Cows Seized by Ketosis

| Test compound | Dosage mg/kg | Measurement item | Change of blood components with time | | | | Change of urine components with time | | | |
|---|---|---|---|---|---|---|---|---|---|---|
| | | | Before adm. | 1 Week after adm. | 3 Weeks after adm. | 6 Weeks after adm. | Before adm. | 1 Week after adm. | 3 Weeks after adm. | 6 Weeks after adm. |
| No. 6 | 50 | Blood sugar level mg/dl | 33.6 | 34.3 | 43.3 | 64.8 | | | | |
| | | Free fatty acids μEq/l | 1,862.3 | 556.6 | 507.5 | 118.2 | | | | |
| | | Acetoacetic acid μmol/l | 1,550 | 1,344 | 608 | 102 | | | | |
| | | Ketone bodies | | | | | +++ | + | − | − |
| No. 4 | 77.2 | Blood sugar level mg/dl | 43.2 | 40.3 | 55.4 | 57.7 | | | | |
| | | Free fatty acids μEq/l | 1,377 | 428 | 303 | 238 | | | | |
| | | Acetoacetic acid μmol/l | 446 | 50 | 142 | 146 | | | | |
| | | Ketone bodies | | | | | +++ | ++ | + | − |
| No. 8 | 100 | Blood sugar level mg/dl | 32.0 | 48.4 | 41.0 | 53.5 | | | | |
| | | Free fatty acids μEq/l | 1,727 | 476 | 747 | 371 | | | | |
| | | Acetoacetic acid μmol/l | 1,232 | 260 | 586 | 76 | | | | |
| | | Ketone bodies | | | | | +++ | + | + | − |
| No. 3 | 25 | Blood sugar level mg/dl | 33.0 | 38.4 | 34.0 | 43.3 | | | | |
| | | Free fatty acids μEq/l | 1,423 | 416 | 306 | 418 | | | | |
| | | Acetoacetic acid μmol/l | 628 | 220 | 816 | 400 | | | | |
| | | Ketone bodies | | | | | +++ | ++ | + | + |
| No. 6 | 25 | Blood sugar level mg/dl | 30.6 | 23.5 | 52.9 | 59.0 | | | | |
| | | Free fatty acids μEq/l | 1,148 | 550 | 201 | 351 | | | | |
| | | Acetoacetic acid μmol/l | 662 | 630 | 156 | 104 | | | | |
| | | Ketone bodies | | | | | +++ | ++ | ± | ± |

Definitions of symbols in TABLE:
+ + + Detected noticeably
+ + Detected clearly
+ Slightly detected
− Not detected

EXAMPLE 1

50 Parts of a compound No. 6, 15.0 parts of light silicic acid anhydride, 5.0 parts of precipitated calcium carbonate, 5.0 parts of corn starch, 2.0 parts of crystalline cellulose, 5.0 parts of a polyvinyl alcohol and 30 parts of water are homogeneously mixed and kneaded. Then, the mixture is ground, pelletized, dried and sifted to prepare granules. The granules are used for curing of ketosis of cows.

EXAMPLE 2

30 Parts of a compound No. 4 and 70 parts of sodium chloride are homogeneously mixed. The mixture is compression-molded to prepare solids. Cows and other livestock are allowed to lick these solids for prevention or cure of ketosis.

EXAMPLE 3

1 Gram of a compound No. 6 is added to 1 kg of a cattle feed. The resulting feed is given to cows or other livestock for prevention or cure of ketosis.

EXAMPLE 4

30 Parts of a compound No. 6, 30 parts of magnesium propionate, 30 parts of calcium carbonate and 10 parts of calcium tertiary phosphate are mixed to prepare a powder. This powder is used for cure of ketosis of cattle and other livestock.

It was also found that a combined use of a compound of the present invention and a nutrient such as glucose, propionic acid or the like further enhances the therapeutic effect of the present invention compound.

What is claimed is:

1. The method for treating or preventing ketosis of cow which comprises administering, during the period from the end of pregnancy to the early stage of lactation, to the cow orally or parenterally an effective amount of a dithia derivative of the formula (I),

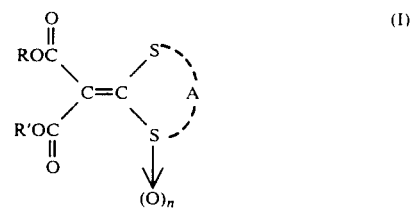

wherein R and R' may be the same or different and are individually a lower alkyl group, n is 0, 1 or 2 and A is a group of the formula —$CH_2$—, in which M is a hydrogen atom or a salt-forming residue, —CH=CH—, —CH$_2$—CH$_2$—,

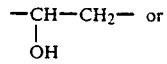

or

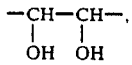

as an active ingredient together with a pharmaceutically acceptable carrier.

2. The method of claim 1, wherein the dithia derivative is a compound of formula (I) wherein R and R' are i—C$_3$H$_7$; A is —CH$_2$—, —CH$_2$—CH$_2$—, —CH=CH$_{13}$

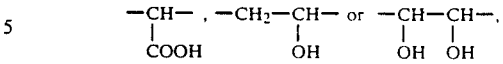

and n is 0 or 1.

3. The method of claim 1, wherein the dithia derivative is diisopropyl 1,3-dithiolan-2-ylidene malonate.

4. The method of claim 1, wherein the dithia derivative is diisopropyl 1,3-dithiol-2-ylidene malonate.

5. The method of claim 1, wherein the pharmaceutically acceptable carrier is feed.

6. The method of claim 1, wherein the amount of dithia derivative administered is 0.1 to 250 mg per 1 kg of the body weight of the animal.

* * * * *